United States Patent [19]

Dorr

[11] Patent Number: 5,565,627
[45] Date of Patent: Oct. 15, 1996

[54] ULTRASONIC EDGE DETECTOR AND CONTROL SYSTEM

[75] Inventor: John A. Dorr, Crofton, Md.

[73] Assignee: Xecutek Corporation, Annapolis, Md.

[21] Appl. No.: 320,993

[22] Filed: Oct. 11, 1994

[51] Int. Cl.⁶ .......................... G01N 29/20; G01N 29/22
[52] U.S. Cl. ................... 73/599; 73/159; 73/611
[58] Field of Search ................ 73/599, 609, 610, 73/611, 612, 159; 226/15, 18, 19, 21; 364/468, 469, 550, 563; 367/118; 318/652

[56] References Cited

U.S. PATENT DOCUMENTS

| | | | |
|---|---|---|---|
| 3,225,988 | 12/1965 | Drenning | 73/599 |
| 4,901,292 | 2/1990 | Schrauwen | 367/118 |
| 4,959,040 | 9/1990 | Gardner et al. | 474/103 |
| 4,963,807 | 10/1990 | Wendling | 318/632 |
| 5,072,414 | 12/1991 | Buisker et al. | 364/550 |
| 5,126,946 | 6/1992 | Ko | 73/159 |

Primary Examiner—Hezron E. Williams
Assistant Examiner—Rose M. Finley
Attorney, Agent, or Firm—Jim Zegeer, Esq.

[57] ABSTRACT

An ultrasonic edge detector system wherein the lateral position of a moving web or sheet is monitored by projecting an ultrasonic beam from a transmitting transducer toward a receiving transducer and the web edge occludes or shadows more or less of the ultrasonic beam changing the ultrasonic energy received by the receiving transducer. Changes in output of the receiving transducer are detected as a measure of change in edge position. Accuracy in the measurement of the position of the edge is achieved by lengthening the path of acoustic energy from the transmitting transducer to the receiving transducer by positioning an acoustic reflector in said path. Reverberations are reduced by causing the angle of incidence of the ultrasonic beam to be at an angle α of greater than 0 degrees. A dual receiving transducer system is disclosed compensating for fluctuations in power to the edge detector system.

7 Claims, 7 Drawing Sheets

ULTRASONIC EDGE DETECTOR AND CONTROL SYSTEM

The present invention relates to improvements in apparatus for automatically locating the position of the edge of a continuous sheet or web of material and, more particularly, to an improved ultrasonic edge detector system for detecting the position of the lateral edge of a strip or web as it moves along a selected path and, still more particularly, to a more accurate measurement and control of position wherein a transmitting transducer emits ultrasonic energy which is shadowed or occluded by the lateral edge of the web or sheet and a receiving transducer is positioned to receive the occluded ultrasonic energy and make a determination of the change in position of the lateral edge of the web or sheet.

There are numerous types of apparatus for automatically tracking the lateral edge of a continuous web or sheet of materials such as paper, plastic, metal or the like, by tracking the displacement of the edge. Such apparatus is necessary in order to maintain optimum sheet quality at a maximum speed of the web or sheet moving in a lengthwise direction and two such systems are disclosed in O'Connor U.S. Pat. No. 3,570,624 and Ko U.S. Pat. No. 5,126,946. In the disclosures of these patents, one or more soundwave paths are provided which are variably attenuated by sidewise displacement of one or more edges of the web or sheet, and the amount and direction of the sidewise displacement or lateral movement of the web or sheet attenuates more or less the sound pulse train to produce a voltage which may be utilized to activate a utilization device such as a recorder, a computer or servo system, or systems to operate machinery to follow the web, all as disclosed in the aforementioned Ko and O'Connor patents.

FIG. 1 corresponds to FIG. 1 of Ko U.S. Pat. No. 5,126,946 and shows a prior art edge detector location system in which transmitter 20, having an ultrasonic emitter 22, emits ultrasound US along a path P past the edge 10 of web or strip B toward receiver 30 which employs a piezoelectric transducer 32. A control network 40 controls the transmitted ultrasonic signal from transducer 22 and processes this signal as it is received by transducer 32 of receiver 30. This process results in a control signal 52 having a value indicative of the edge position for controlling, for example, a mechanical feedback system illustrated as a position servo 50 to correct the edge position. The voltage on line 52 determines the magnitude and direction of correction by servo 50 to reposition edge 10 in path P and a feedback or servo network arrangement. As the lateral edge 10 occludes or shadows more of the ultrasonic signal US, less energy impinges upon transducer 32 and the amount of energy impinging upon the transducer 32 is converted to a value or magnitude of the control signal which is used to provide a corrective direction signal.

In the Ko patent, the receiver is spaced from the transmitter a predetermined distance causing the pulses to be received by the receiver at a given time after transmit signals for a given ambient temperature. The control system 40 includes a means creating a logic window having a given time base length and occurring at a time after a transmit signal with the said time being slightly less than the given time whereby each of the electronic signals occurs at an offset time in the logic window.

FIG. 1 of Ko patent shows a precisely defined occluded or shadow zone behind the web 10 which, as a practical matter, is not achievable and is believed to be the most significant problem with ultrasonic edge detectors or locators of this type. Ignoring diffraction (which also tends to complicate the problem), FIG. 1B shows that the ultrasound should be presented as a series of ray paths. Note that the paths into the previously depicted shadow or occluded zone can be out of phase with the direct ray paths and reduce the response of the receiver 32. Moreover, if the web or sheet should move from the depicted centerline position (i.e., closer to one of the transducers 22 or 32), then the out-of-phase components change as does the response of the receiver 30. Note that the ray paths are the same and independent of any spacing.

The present invention is directed to solving these problems.

Ideally, the ultrasonic wave impinging on the web should be planar, being generated by a far-off transmitting transducer. Then, the angle of rays into the "shadow zone" would be quite small, and the out-of-phase rays would not contribute much to the response nor change much with small changes in the web position. Consequently, according to the present invention, there are at least four things that can be done to solve this problem:

1. Locate one transducer farther from the web.
2. Locate the other transducer closer to the web.
3. Reduce the aperture size of the most distant transducer.
4. Increase the wavelength of the ultrasound.

In a first embodiment of the present invention, a reflector is utilized to enable greater separation between the transmitting and receiving transducers without increasing the width of the assembly. Alternatively, the transducer 22 could be replace with an assembly as described in applicant's U.S. Pat. No. 4,530,077 to achieve a reduction in aperture with no loss in efficiency. The aperture can also be reduced by masking-off a Polaroid™-type transducer to provide a narrower radiating face.

A second improvement is to increase the angle the acoustic wave front makes with the web to thereby reduce reverberation. In this case, the aperture of the receiving transducer must be sized to be responsive at the new angle.

In a further feature of the invention, the problem of changes in the receiver sensitivity and transmitter output due to fluctuation in power supply voltage resulting in erroneous detector output is solved.

In a further embodiment of the invention, the transmitter's transducer also serves as a receiving transducer and an acoustic target is provided with the return signal from the target being used to provide a gate signal for the receiving transducer circuitry and compensates for variations due to wavelength changes with air temperature.

DESCRIPTION OF THE DRAWINGS

The above and other objects, advantages and features of the invention will become more apparent when considered with the following specification and accompanying drawings wherein.

Figure 1A:
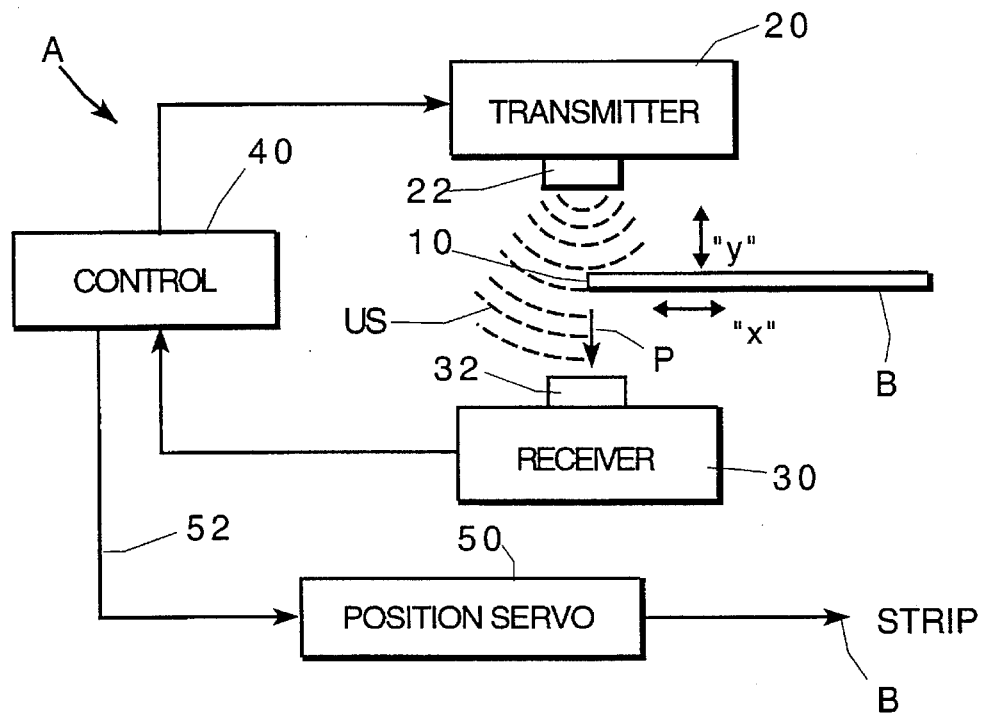
FIG. 1A is an excerpt from FIG. 1 of Ko U.S. Pat. No. 5,126,946 showing a prior art edge detector system, FIG. 1B (prior art) shows the ultrasound waves as a series of ray paths.
Figure 1B:
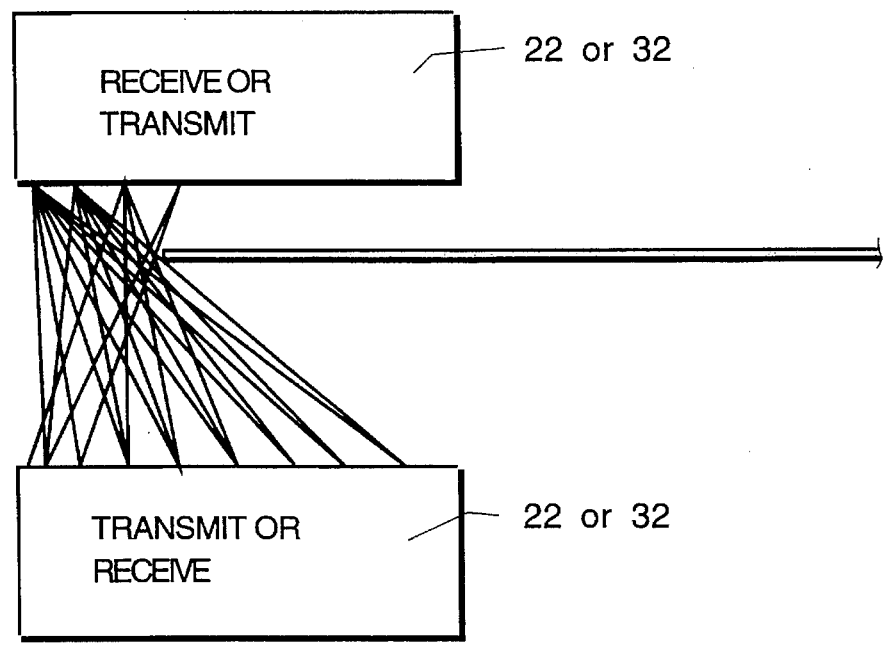
Figure 2A:
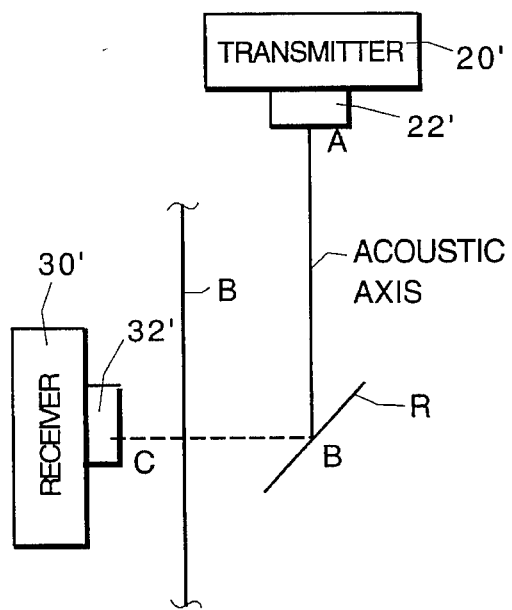
FIG. 2A is a side elevational view of one embodiment of the invention.
Figure 2B:
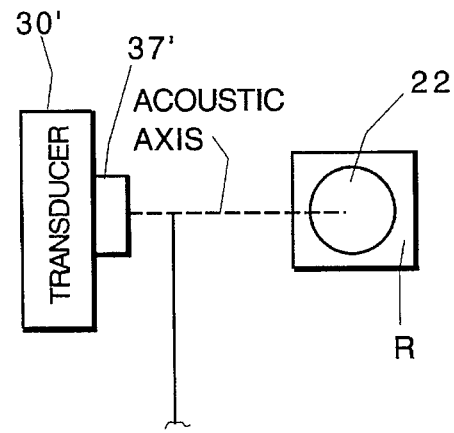
FIG. 2B is a plan view of a vertical web detector of the embodiment shown in FIG. 2A.

DETAILED DESCRIPTION OF THE INVENTION:

Referring now to FIGS. 2a and 2b, a greater separation or spacing between the transmitter transducer 22' and the web or sheet B and the receiving transducer 32' is provided by reflector R so that the path length is AB+BC making the ultrasonic wave front impinging on the web essentially planar, having been generated by a far off transmitter transducer 22'. In this way, the angles of rays into the shadow or occluded zone would be small and the out-of-phase rays would not contribute much to the response nor change much with small changes in the web position. Thus, the ultrasonic reflector R enables a greater separation between the web and the transmitter transducer 22' without increasing the width of the assembly.

Alternatively, the transducer 22' could be replaced with an assembly as described in Dorr U.S. Pat. No. 4,530,077 to achieve a reduction in aperture with no loss in efficiency. Another way of reducing the transmitter aperture would be to use a Polaroid™-type transducer and mask-off the Polaroid™ transducer to provide a narrower radiating face.

Figure 3:
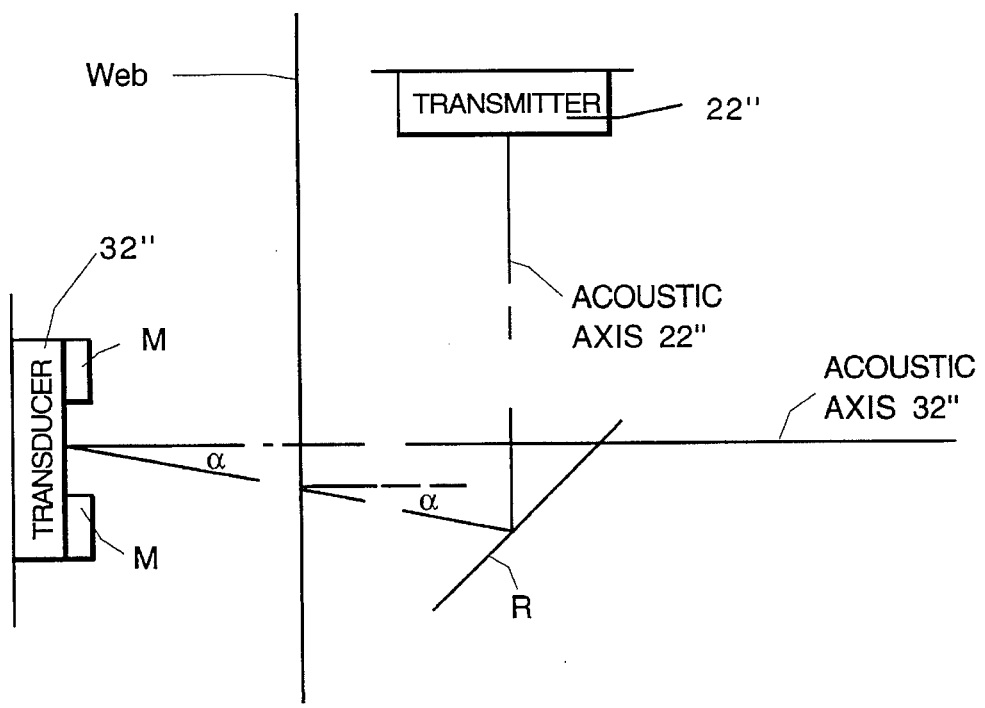
FIG. 3 is a side elevational view of a further embodiment of the invention.

Referring now to FIG. 3, the angle α that the acoustic axis makes with the web is made to be other than 0 degrees to thereby reduce reverberations. In this case, the receiving aperture 32" has its aperture sized (by masking M and the like) to be responsive at the new angle α (within the 3 dB beam width of the receiver transducer 32").

The angle α is preferably within the −3 dB angular response pattern of the receiving transducer pattern (32") of FIG. 3. For example, if 32" represents an edgewise-viewed Polaroid™ electrostatic transducer and the top and bottom of 32" are masked M off to limit the aperture to the central 0.6 inch, then the 50 kHz −3 dB beamwidth is approximately 24 degrees and α should be no more than about 12 degrees.

Whenever the power supply voltage fluctuates, there is a change in the receiver's sensitivity and a change in the transmitter power output. To eliminate this source of error, the receiver arrangement shown in FIG. 4 and its accompanying block diagram shown in FIG. 5 can be utilized. In this arrangement, a pair of receiving transducers 32R-1, 32R-2 angled θ relative to each other with the acoustic axis AA being along the point X between the two transducers 32R-1 and 32R-2. The web or sheet B is normally positioned to be normal to the acoustic axis of transducer 32R-1 in the initial or set-up position with the edge of the web B positioned as shown. The outputs of the receivers 32R-1 and 32R-2 are amplified in amplifiers A1, A2, with the output of the amplifiers A1 and A2 being applied to level detectors LD1 and LD2, respectively. The output of level detector LD2 is passed through a divide-by-two circuit D-2 and the output from the level detector LD1 and divide by 2 circuit D-2 being applied to subtraction circuit S1, the gain of amplifier A2 is adjusted to zero the output when the web is in the preferred center position relative to receiver 32R-1. Thereafter, as the web or sheet B moves, any changes in the lateral position of the edge E1 produces a positive or negative voltage output from the subtraction circuit S1 which output is directly proportional to the changes in the lateral position of the web edge El. In some embodiments the subtraction circuit can be a compare circuit.

Figure 4:
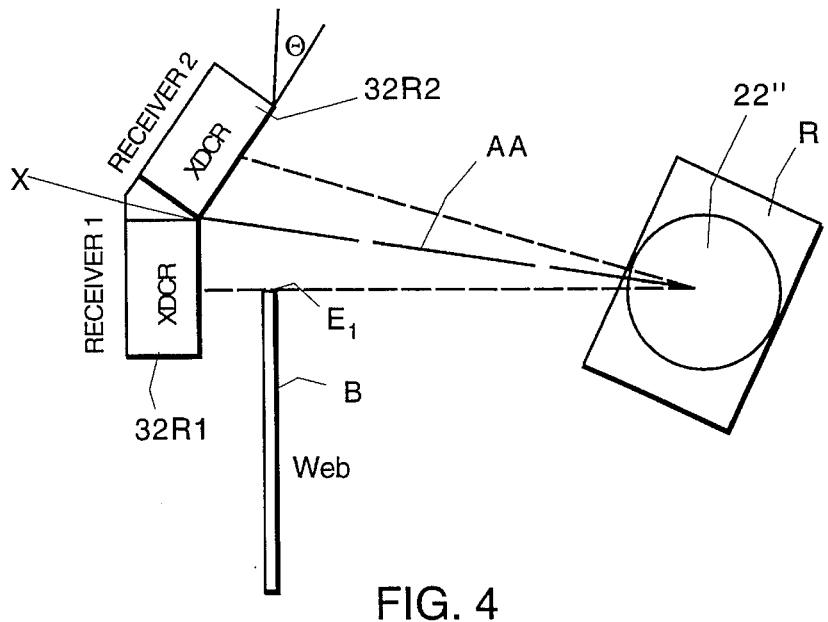
FIG. 4 is a side elevational view of a further embodiment of the invention.
Figure 5:
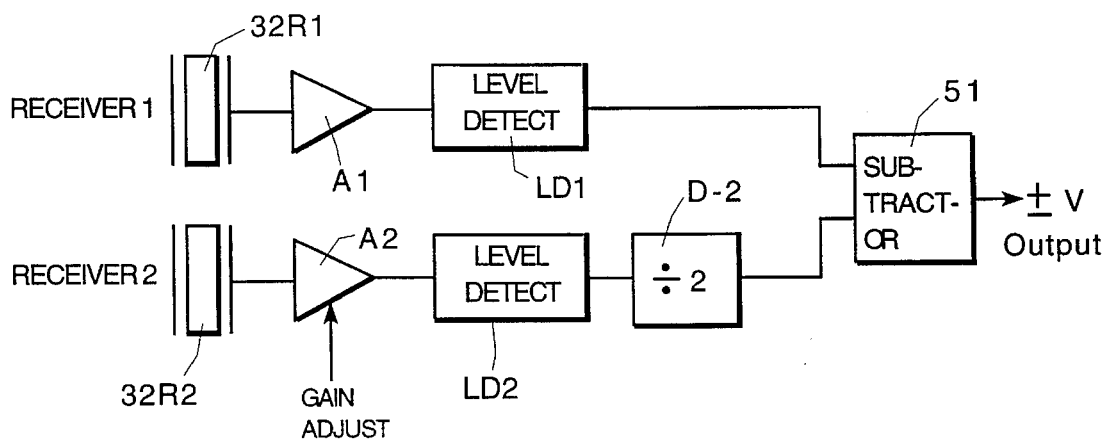
FIG. 5 is a block diagram of a circuit used with the transducers of FIG. 4 which addresses the problems of changing receiver sensitivity and transmitter output due to fluctuations in power supply voltage.

The arrangement shown in FIGS. 4 and 5 therefore eliminates the problem of changing receiver sensitivity and transmitter output due to fluctuations in the power supply voltage thereby resulting in a more accurate detector output.

The preferred systems shown in FIGS. 2–5 are continuous wave or CW systems. Referring now the pulse system shown in FIG. 6A, the arrangement is similar to the arrangement shown in FIG. 2A, except in this case, a target is positioned at a predetermined distance C from the transmitting transducer 22" which, in this case, is also adapted to receive echoes from the target T.

Figure 6A:
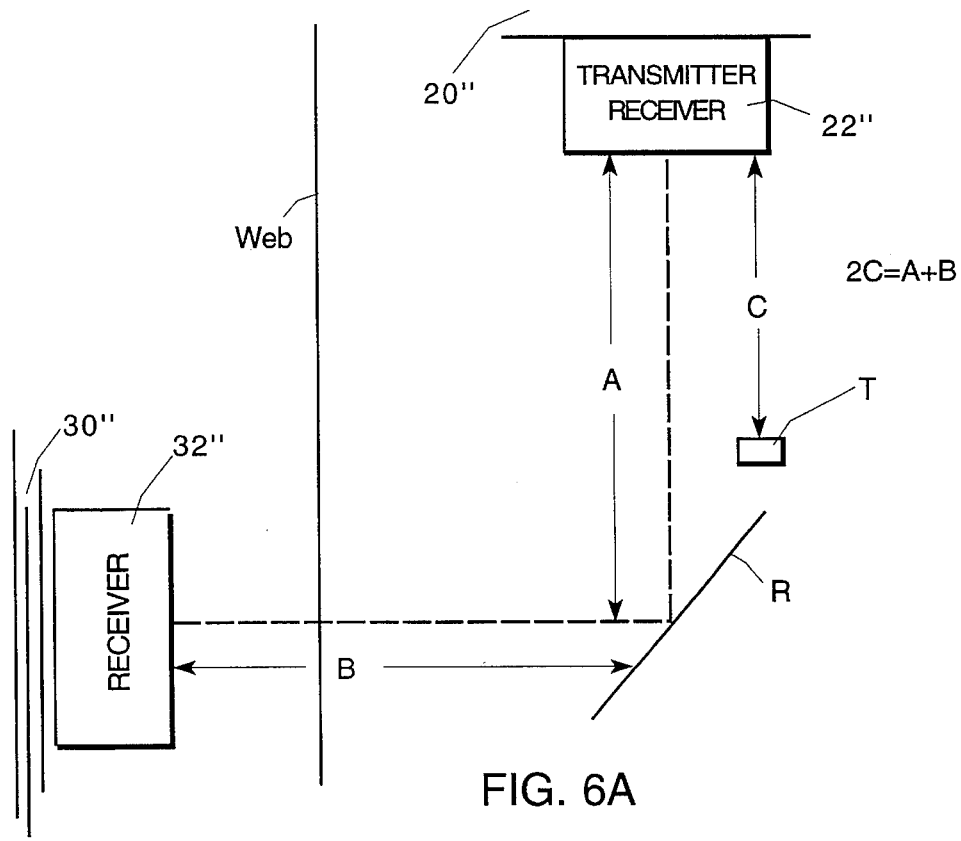
FIG. 6A is a side elevational view of a further embodiment of the invention.
Figure 6B:
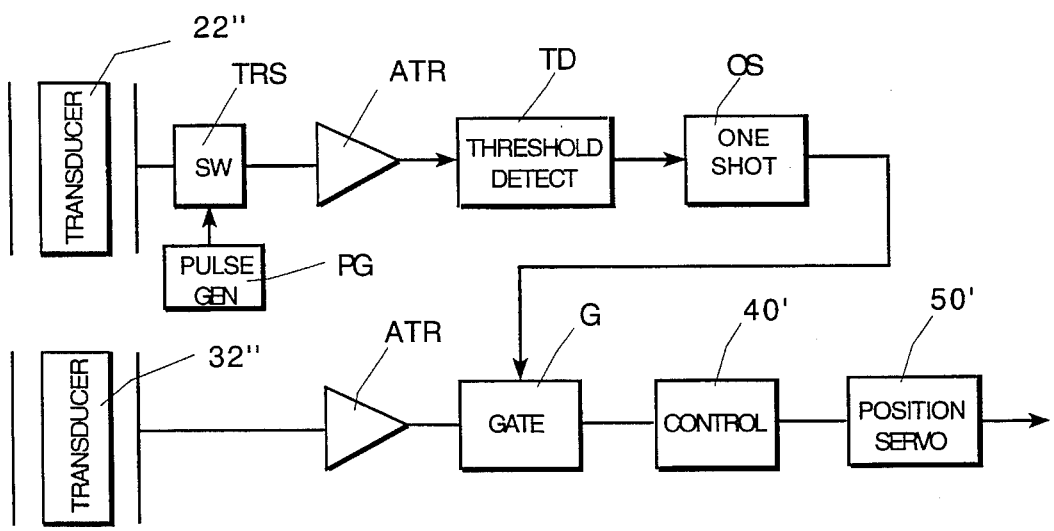
FIG. 6B is a block diagram of a circuit used with the embodiment of FIG. 6a, FIG. 7 is a block diagram of a pulsed version of the system shown in FIG. 4, and FIGS. 8A and 8B are top plan and side elevational views of a further embodiment.

As shown in FIG. 6B the transmit receive transducer is energized by a pulse generator PG via transmit receive switch TRS and supplies its output through an amplifier ATR to a threshold detector TH which supplies its output to a one shot circuit OS which in turn produces an open gate signal the time being the equivalent of twice the distance C (e.g., 2×C) and the distance to and from target T from transmitter receiver TR. The receiver operates as before except that the output from the amplifier ATR is applied through a gate circuit G which is opened according to the gate control signal from the one shot OS. The output from the gate circuit is connected to the control circuit as described earlier.

Figure 7:
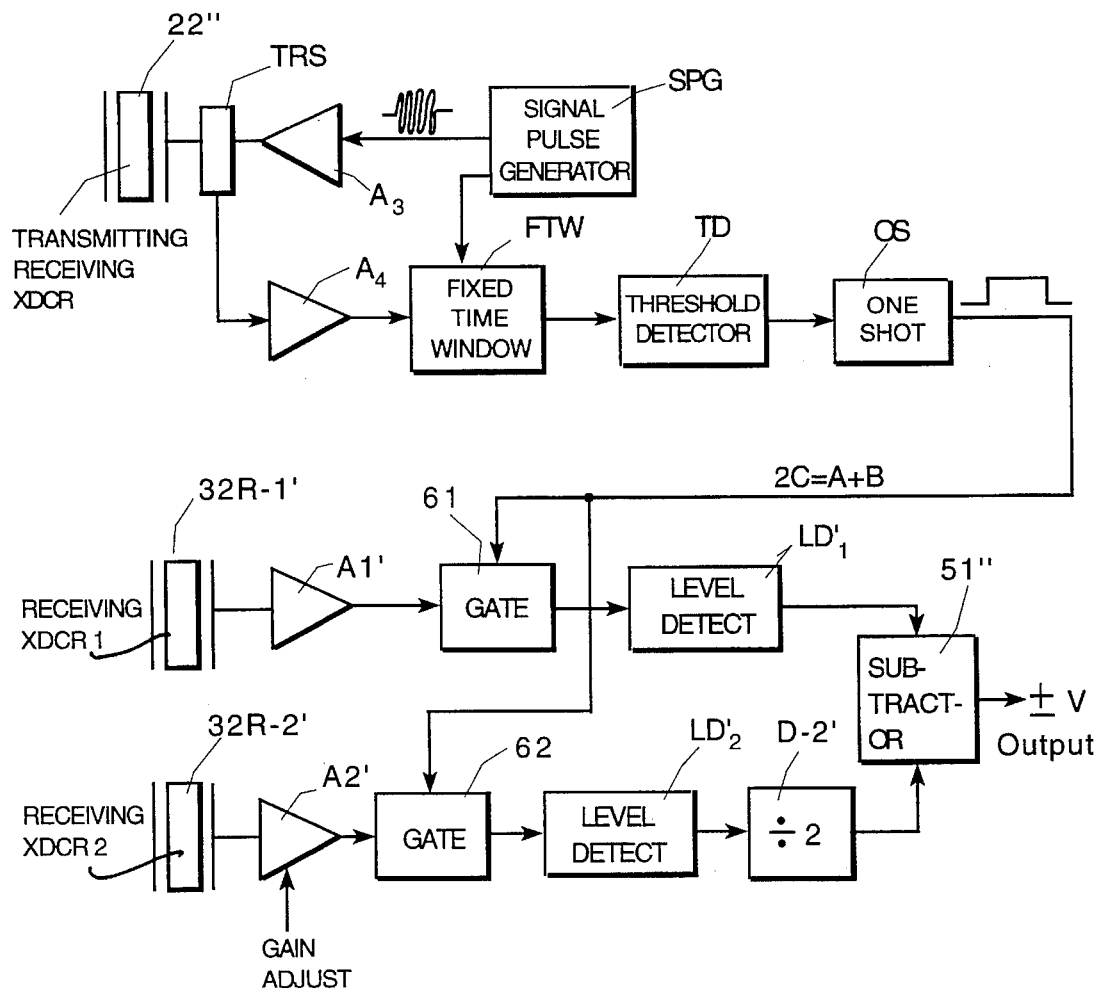

A further embodiment of the invention expands on the pulsed system shown in FIGS. 6A and 6B is illustrated in FIG. 7. In this case, receiving transducers 32R-1' and 32R-2' and their associated processing circuits are as shown in FIG. 5, and gate circuits G1 and G2 provided in the respective signal paths. Transmit/receive transducer 22''' is energized by a pulse provided by power amplifier A3 and signal pulse generator SGP via transmit receive switch TRS. Echoes from a target T (FIG. 6A) are amplified by amplifier A4 and passed by fixed time window FTW, the window being set by a window start pulse from signal pulse generator SGP. The output of window circuit FTW is threshold detected in detector TD and applied to trigger one shot circuit OS. The output corresponds to twice the distance C to target T which is substantially equal to the sum of the distance from the transmit/receive transducer to reflector R and from reflector R to transducer 32".

Figure 8A:
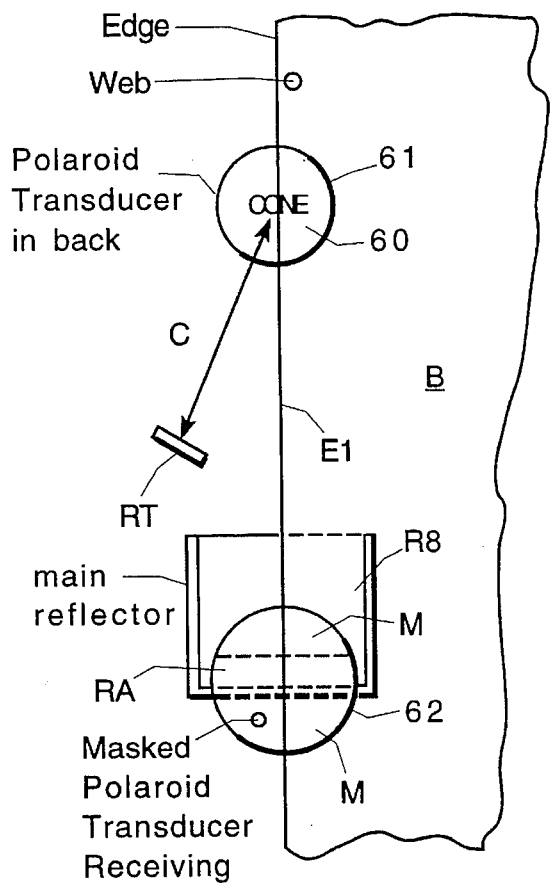
FIG. 8C is a block diagram of the circuit used in this embodiment.
Figure 8B:
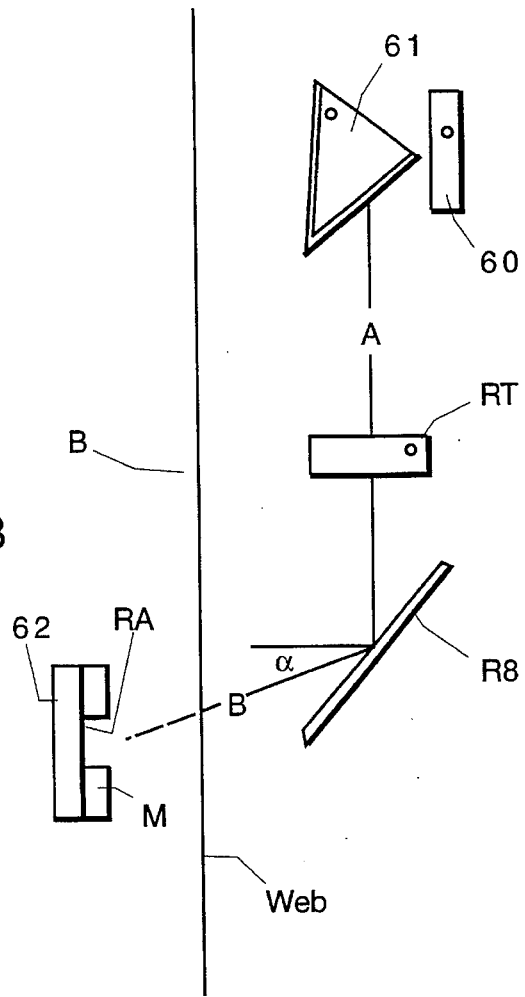
Figure 8C:
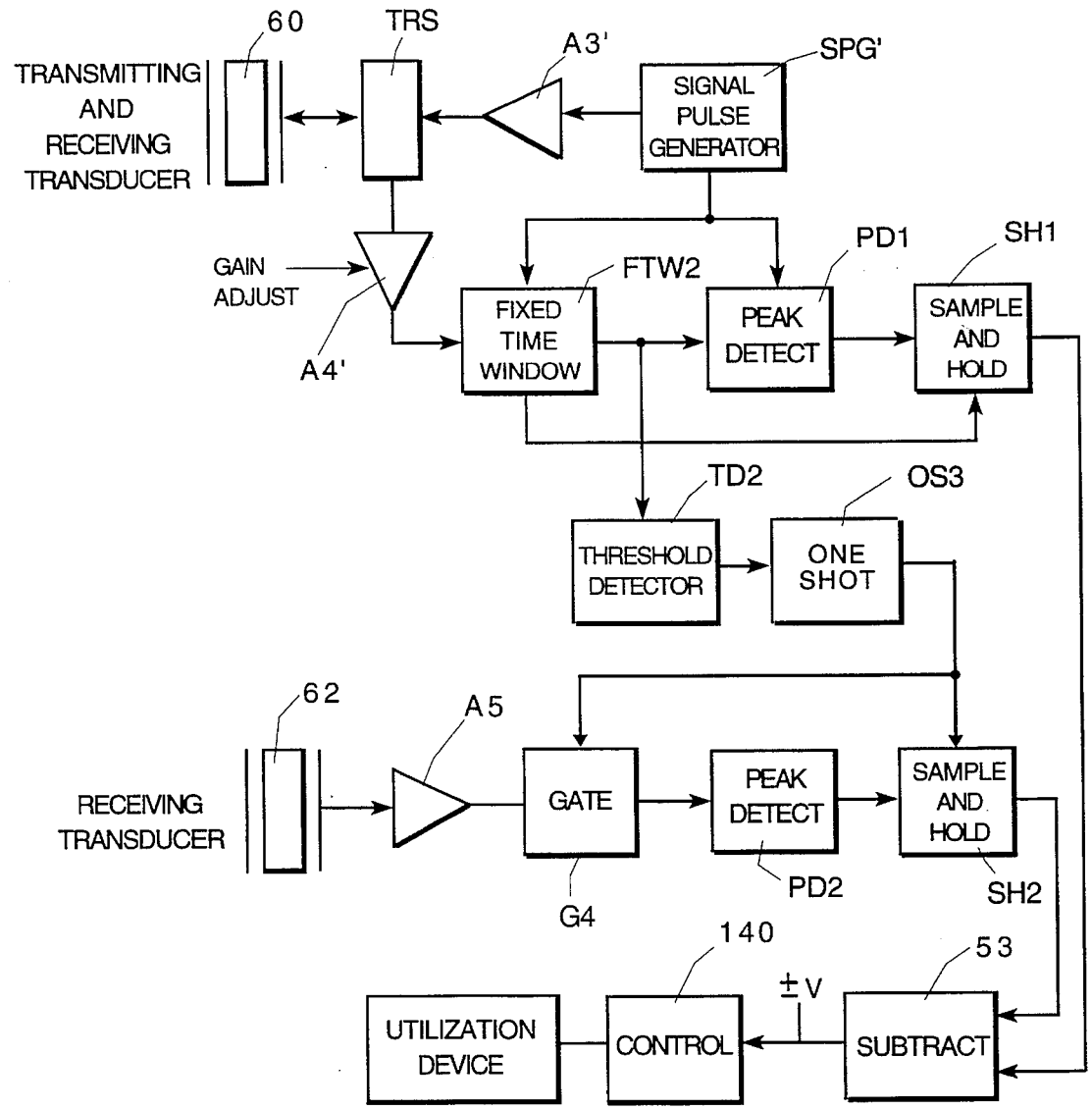

In the embodiment shown in FIGS. 8A, 8B and 8C, a Polaroid™-type transducer 60 transmits pulses of ultrasonic energy on conical beam transformer 61 which expands and directs the ultrasonic energy along path A to acoustic reflector R8. (Reference is made to my U.S. Pat. No. 4,530,077 which discloses producing a wide beam width (narrow effective aperture) which is incorporated herein by reference.) Reflector R directs the acoustic energy along path B at an angle α to a line normal to the plane of the sheet or web B. Receiving transducer 62 is a Polaroid™ transducer is which masked M to achieve an approximately rectangular receiving aperture RA for better output linearity.

Side reference reflector target RT provides both gating pulse and reference level output. These compensate for both (1) power supply fluctuations, and (2) signal level variations due to wave length change with air temperature. As shown in FIG. 8C, signal pulse generator SGP' supplies an ultrasonic pulse signal to power amplifier which in turn is coupled to transmit/receive transducer 60 via transmit/receive switch TRS'. Signals reflected off of side reference reflector target RT are reflected off of cone 61 received by transmitting and receiving transducer 60 and coupled to amplifier A4' to fixed time window circuit FTW2, which receives a start pulse from pulse signal generator SGP' and outputs an analog echo signal pulse to threshold detector TD2 and peak detector PD1, which also receives the pulse from signal generator SGP'; and, in turn, outputs a peak signal to sample out hold circuit SH1. A control signal from fixed time window FTW2 control the outputting of the peak signal from sample and hold SH1 to subtract (or compare) circuit 53.

Ultrasonic energy received by a receiving transducer 62 is coupled by amplifier A5 to gate circuit 64 which is gated open (as in FIG. 7) by a gate signal from one shot circuit OS3. The gated signal from gate G4 is peak detected in peak detector PD2 whose output is sampled by sample and hold circuit SH2 which is also controlled by the signal from one shot circuit OS3. The difference signal (±V) from subtract (or compare) circuit S3 is thus compensated for both power supply fluctuations and signal level variations due to wavelength change with air temperature.

Although the invention has been described in analog terms, it will be appreciated that analog or digital circuits may be used.

While the invention has been described with several embodiments and adaptations thereof, it will be appreciated that various adaptations and modifications to the invention will be readily apparent to those skilled in the art.

What is claimed is:

1. In an ultrasonic edge detector system for detecting the lateral edge of a moving web wherein a transmitting transducer is positioned to transmit a pulse toward the path of said lateral edge of said web such that said lateral edge occludes a receiving transducer means positioned to receive said pulse, said receiving transducer means being activated a preselected time after the transmitting transducer emits a pulse, and circuit means connected to said receiving transducer for providing a signal corresponding to the degree of occluding of said receiving transducer means by said lateral edge, each said receiving transducer means and said transmitting transducer having an acoustic axis, the improvement comprising said transmitting transducer having its acoustic axis oriented such as to have a vector component parallel to the plane of said web, and an ultrasonic reflector having a reflection axis positioned relative to said path of said edge and acoustic axis of the receiving transducer means such that acoustic energy reflected off of said ultrasonic reflector is received by said receiving transducer means and there is a greater acoustic separation between said receiving transducer means and said transmitting transducer to reduce reverberations.

2. The ultrasonic edge detector system defined in claim 1 wherein said reflection axis of said reflector is not axial with said receiving transducer means, and said receiving transducer means having an aperture, said aperture being sized to be responsive to the angle between said receiving transducer means and the reflection axis of said reflector.

3. The ultrasonic edge detector system defined in claim 1 wherein said receiving transducer means is constituted by first and second transducers contiguous to each other to define the acoustic axis of said receiving transducer means, said circuit means including a first circuit connected to said first receiving transducer for providing a first output signal, said first circuit including a gain adjustable circuit, a level detector and a divide by two circuit, said circuit means further including a second circuit connected to the second receiving transducer for providing a second output signal, said second circuit including an amplifier and a second level detector circuit, a subtraction circuit connected to receive said first and second output signals, said gain adjustable circuit of said first circuit being adjusted so that in a predetermined position of said lateral edge the output of said subtraction circuit is zero and deviation of said lateral edge from said predetermined position produces proportionate changes in the output of said subtraction circuit.

4. The ultrasonic edge detector system defined in claim 1 including a reflective target positioned at a distance C from said transmitting transducer and between said reflector and said transmitting transducer and wherein said transmitting transducer is adapted to receive ultrasonic echoes from said reflective target and produce a gate signal, a gate circuit connected to the output of said receiving transducer means, and means connecting said gate signal to any output of said gate circuit to control the output of said receiving transducer means.

5. In an ultrasonic edge detector system wherein the lateral position of a moving web or sheet is monitored by projecting an ultrasonic beam from a transmitting transducer along a path toward the edge and said edge occludes more or less of said ultrasonic beam upon a receiving transducer, said path having a given length, and measuring changes in output of said receiving transducer as a measure of change in edge positions the method of improving accuracy in the measurement of the position of said edge comprising lengthening said path from said transmitting transducer to said receiving transducer beyond said given length, and the lengthening of said path is achieved by an acoustic reflector positioned in said path.

6. In an ultrasonic edge detector system wherein the lateral position of a moving web or sheet is monitored by projecting an ultrasonic beam from a transmitting transducer along a path toward the edge of said moving web or sheet and said edge occludes more or less of said ultrasonic beam upon a receiving transducer, said path having a given length, and measuring changes in output of said receiving transducer as a measure of change in edge position, the method of improving accuracy in the measurement of the position of said edge comprising lengthening said path from said transmitting transducer to said receiving transducer beyond said given length, and transmitting said ultrasonic beam at an acute angle $\alpha$ of incidence to said moving web greater than 0 degrees to reduce reverberations.

7. The invention defined in one of claims 5–6 including compensating for fluctuations in power to said edge detector system.

\* \* \* \* \*